United States Patent
Kirby et al.

(10) Patent No.: US 7,556,038 B2
(45) Date of Patent: Jul. 7, 2009

(54) SYSTEMS AND METHODS FOR CONTROLLING BREATHING RATE

(75) Inventors: Todd Kirby, Spring Church, PA (US); Leonardo A. Baloa, Pittsburgh, PA (US); Erik K. Witt, Murrysville, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/836,292

(22) Filed: Aug. 9, 2007

(65) Prior Publication Data

US 2008/0035147 A1 Feb. 14, 2008

Related U.S. Application Data

(60) Provisional application No. 60/837,205, filed on Aug. 11, 2006.

(51) Int. Cl.
*A62B 7/00* (2006.01)

(52) U.S. Cl. .............................. 128/204.21; 128/204.18; 128/204.23

(58) Field of Classification Search ............ 128/204.18, 128/204.21, 204.23, 204.24, 205.24

See application file for complete search history.

(56) References Cited

U.S. PATENT DOCUMENTS

| | | | | |
|---|---|---|---|---|
| 4,637,385 A | * | 1/1987 | Rusz | ...................... 128/204.21 |
| 5,800,337 A | | 9/1998 | Gavish | |
| 5,937,853 A | * | 8/1999 | Strom | ................... 128/204.23 |
| 6,105,575 A | | 8/2000 | Estes et al. | |
| 6,532,957 B2 | * | 3/2003 | Berthon-Jones | ........ 128/204.21 |

* cited by examiner

*Primary Examiner*—Steven O Douglas
(74) *Attorney, Agent, or Firm*—Timothy A. Nathan

(57) ABSTRACT

A method and corresponding system for providing breathing cues includes monitoring respiration of a user and determining a user breathing frequency including an inspiration portion and an expiration portion of the breathing, supplying a high positive air pressure to the user during the inspiration portion and a low positive air pressure during the expiration portion in substantial synchronicity with the user's respiration, comparing the user breathing frequency with a target breathing frequency, and when the user breathing frequency is greater than the target breathing frequency, increasing, in a predetermined manner, a time over which the high positive air pressure is supplied to the user, and adjusting a time over which the low positive pressure air pressure is supplied to the user.

23 Claims, 4 Drawing Sheets

SYSTEMS AND METHODS FOR CONTROLLING BREATHING RATE

CROSS-REFERENCE TO RELATED APPLICATIONS

This application claims priority under 35 U.S.C. § 119(e) from provisional U.S. patent application No. 60/837,205 filed Aug. 11, 2006 the contents of which are incorporated herein by reference.

BACKGROUND OF THE INVENTION

1. Field of the Invention

The present invention relates generally to systems and methods for controlling the breathing rate of a patient. More specifically, embodiments of the present invention are directed to controlling the application of air pressure (e.g., in a bi-level positive air pressure system) to assist a patient with reducing his/her breathing rate.

2. Description of the Related Art

Hypertension is a significant problem in nearly all western cultures and is an underlying cause for stroke and heart attack. Termed the "Silent Killer," hypertension affects approximately 1 in 4 Americans, and occurs with even higher prevalence in some European communities. Hypertension is also gaining recognition as a co-morbid factor in obstructed sleep apnea (OSA) patient populations, with recent studies indicating that as many as 80% of patients seeking treatment for OSA may unknowingly suffer from this disease.

Slower breathing has been shown to effectively reduce hypertension.

Indeed, a focus of techniques such as Yoga and Qigong is to slow a person's breathing to effectively relieve stress and lower blood pressure. In recent years, the physiological mechanisms underlying this response have been shown to involve changes in the autonomic nervous system through the following chain of events:

The process of slow breathing requires the autonomic nervous system to make more frequent adjustments in blood pressure.
In response to these frequent changes, the autonomic nervous system becomes more sensitive to BP changes (via the baroreflex).
The baroreflex becomes amplified.
In order to better regulate BP, a readjustment of central neural control occurs by increasing vagal activity and inhibiting sympathetic activity, both of which act to reduce BP.

Several studies support the idea of using slower breathing to reduce blood pressure in hypertensive individuals. Currently, one device on the market (RESPeRATE by Intercure™ (Fort Lee, N.J.)) is FDA approved for the treatment of hypertension. The RESPeRATE device is designed to act as a breathing "coach" by using audiovisual cues to guide the user to a slower breath rate.

The operation of this device is described, at least in part, in U.S. Pat. No. 5,800,337 to Gavish. Gavish discloses a system for modifying naturally occurring biorhythmic activity by changing at least one "non-frequency" characteristic of input to the user in response to changes in the biorhythmic activity of the user. A focus of Gavish is to effect absolute and relative durations of portions or segments of an overall biorhythmic pattern, such as breathing, independently of changes in the overall frequency of the user's biorhythm being monitored (again, e.g., breathing). The input to the user that is disclosed by Gavish includes audio, visual or tactile cues.

While still other biorhythmic feedback methodologies are known, there is nevertheless a need for different approaches to effect the breathing rate or frequency of a patient to induce, among other things, lower blood pressure, or simply induce improved periods of relaxation.

SUMMARY OF THE INVENTION

Described herein is a methodology, generally referred to as the paced breathing (PB) method, for helping patients breathe at a therapeutic rate through the use of positive pressure cues to, among other things, reduce their blood pressure.

An aspect of the invention is to employ positive air pressure (PAP) cues from a suitable device such as a Bi-Level PAP (BiPAP) device available from Respironics (Murrysville, Pa.) as a more natural proprioceptive signal to coach patients to breathe at a slow, therapeutically significant breath rate (e.g., <10 breaths per minute (BPM)). The methodology disclosed herein provides a drug-free way for some patients to reduce their blood pressure, among other physiological benefits.

In one possible implementation, a method is provided that monitors the respiration of a patient or user to determine the user's breathing or respiration frequency.

Respiration can be considered to comprise an inspiration portion or time and an expiration portion or time. During the inspiration portion of the user's respiration a HI pressure of the Bi-level PAP is supplied, and during the expiration portion, the LO pressure of the Bi-level PAP is supplied. The user's breathing frequency is then compared to a target breathing frequency. When the user's breathing frequency is greater than the target frequency, the time over which the HI pressure of the Bi-level PAP is supplied is increased, in a predetermined manner, and the time over which the LO pressure of the Bi-level PAP is supplied is adjusted. The LO pressure time may be adjusted in accordance with a fixed ratio between the HI and LO pressure times, or may be adjusted to coincide with the user's actual expiration time. Those skilled in the art will appreciate that aside from positive air pressure, one or more of the pressure cues may be positive, negative, or atmospheric.

The methodology described herein may also maintain a counter or timer to track the amount of therapy time the user has had over a predetermined period of time, e.g., over a given week. While not critical, this may indeed be an important feature since there is a reported threshold of 180 minutes of slow breathing across an 8 week period for some breathing therapies to be effective. Therapy data can be stored and reported using, e.g., well-known SmartCard technology.

Another possible implementation might include the use of a blood pressure cuff (sphygmomanometer) in conjunction with a Bi-PAP device to track and report blood pressures using the same reporting technologies found in conventional xPAP machines.

Additional Effects

It is possible that the methodology and device for inducing slow breathing described herein may have effects outside of hypertension. Similar baroreflex sensitivity changes have been observed with changes in pain, and thus the device may have hypoalgesic effects. With the associated autonomic influences, this therapy may eventually be shown to benefit additional disorders including:

Migraine
Anxiety (and Stress)
Restless Legs Syndrome
Obesity

Chronic Fatigue/Fibromyalgia
Mood Disorders
Slow Patterned Breathing During Birth Labor These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Embodiments of the present invention have the capacity to reduce the breath rate of a patient using a positive pressure device. A positive pressure device is well-known and is disclosed, for example, in U.S. Pat. No. 6,105,575, hereby incorporated by reference in its entirety. In this same field, continuous positive airway pressure (CPAP) has been used for many years and has proven to be helpful in promoting regular breathing. Inspiratory positive air pressure (IPAP), of which bi-level positive air pressure (BiPAP) is a category, has also been known. In BiPAP, two levels of positive air pressure (HI and LO) are supplied to a patient. Properly controlling the timing of the HI and LO segments of BiPAP in accordance with the principles of the present invention can more effectively assist a patient in reducing his/her breathing rate.

In this regard, and in accordance with an embodiment of the present invention, the paced breathing (PB) method and related system (collectively referred to herein as "the PB method") first measures the breath rate of the patient and then determines an optimal "machine inspiration time" ($T_{insp}^{M}$) and "machine expiration time" ($T_{exp}^{M}$) to act as a breathing "coach." The $T_{insp}^{M}$ and $T_{exp}^{M}$ correspond to the application of HI or LO pressure to the patient in the context of BiPAP therapy. By setting $T_{insp}^{M}$ and $T_{exp}^{M}$, the PB method may help to control or effect the breathing frequency of the patient. In control terms, the patient's breath rate is the measured variable ($BR_p$) and the periods of inspiration and expiration ($T_{insp}^{M}$ and $T_{exp}^{M}$) are the control variables used for feedback control of breath frequency.

Figure 1:
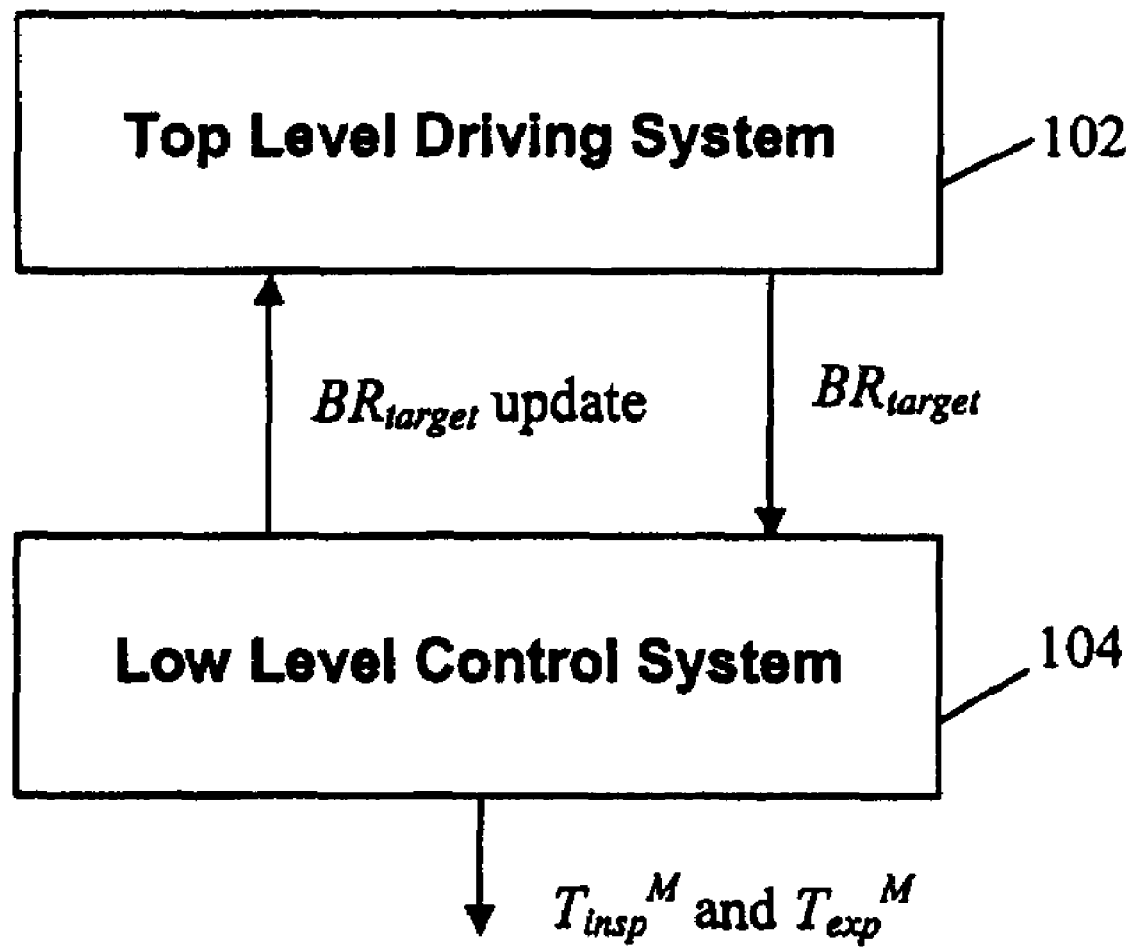
FIG. 1 depicts an exemplary system architecture for the PB method in accordance with an embodiment of the present invention.

The PB method is preferably comprised of two levels of control, but those skilled in the art will appreciate that the methodology described herein may be implemented as a single programming module, or broken up into still greater numbers of modules or levels of control. As shown in FIG. 1, there is provided 1. a Top Level Driving System (TLDS) 102 in which the target breath rate is set, and
2. a Low Level Control System (LLCS) 104 that uses the target breath rate ($BR_{target}$) as input and sets a machine inspiration and expiration time ($T_{insp}^{M}$ and $T_{exp}^{M}$) according to predetermined control logic. Feedback is provided to TLDS 102 through the variable $BR_{target}$ Update (discussed below).

In accordance with one embodiment, and as explained below, the periods of inspiration and expiration ($T_{insp}^{M}$ and $T_{exp}^{M}$) are preferably set at a fixed ratio, regardless of breath rate, such that the variable for feedback control of the patient's breathing is breath frequency. During instances when the patient may be slowing his/her breath rate more quickly than the machine's targeted breath rate, TLDS 102 updates its target breath rate via a command (i.e., $BR_{target}$ Update) sent by LLCS 104.

Top Level Driving System

Figure 2:
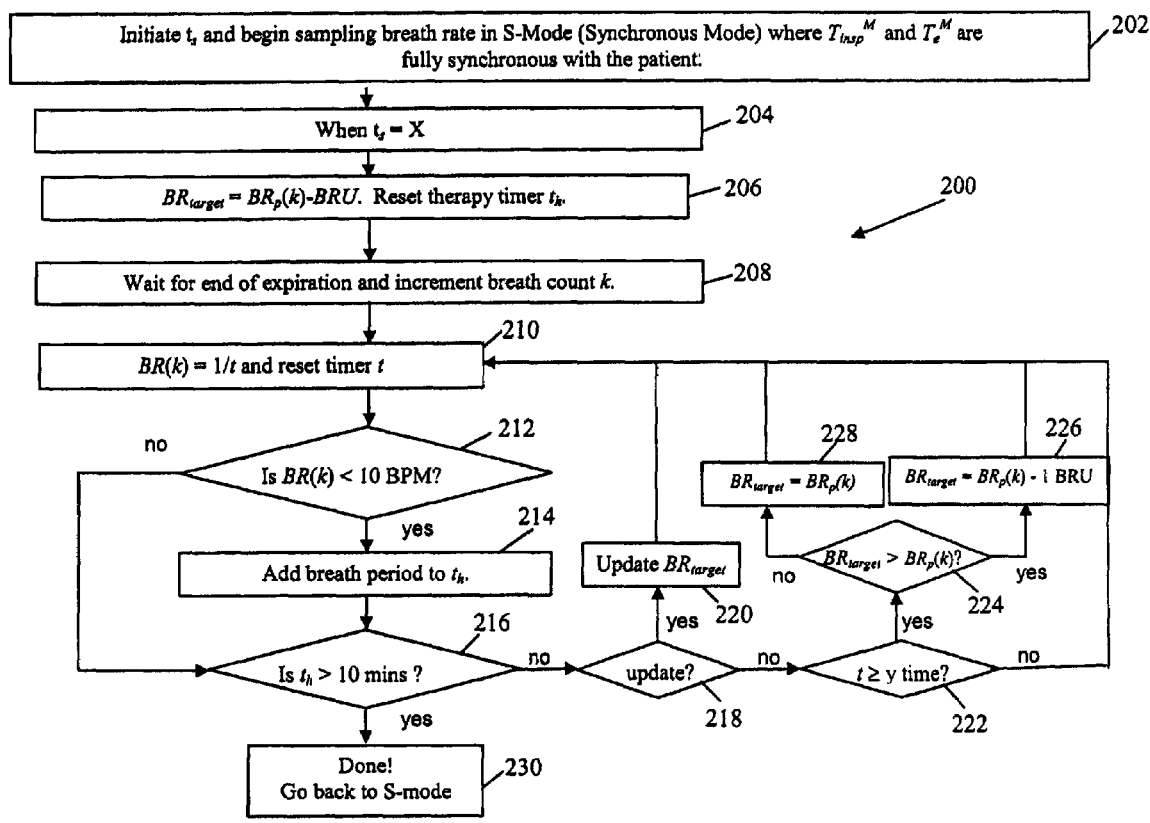
FIG. 2 is an exemplary sequence of instructions performed by a top level driving system (TLDS) in accordance with an embodiment the present invention.

An overall objective of TLDS 102 is to drive the patient's breathing ($BR_p$) to the lowest reasonable frequency for, e.g., at least 10 minutes. TLDS 102 operates to reduce the patient's breath rate by stepping down the target breath rate ($BR_{target}$) and sending this value to the low level control system (LLCS) 104. TLDS 102 determines the rate at which the patient should be breathing and LLCS 104 responds to $BR_{target}$ by setting control variables ($T_{insp}^{M}$ and $T_{exp}^{M}$). FIG. 2 depicts a flow diagram showing the sequence of instructions to step down the target breath rate to assist in coaching a patient to breath more slowly.

Variables depicted in FIG. 2 are defined as follows:
$t_s$—time spent in Synchronous (S) Mode
$BR_{target}(k)$—target breath rate
$BR_p(k)$—average patient breath rate
$BR(k)$—instantaneous breath rate
t—time spent at current breath rate
$t_h$—total therapy time
X—sampling period in S-mode
y—max time allowed at current breath rate
$T_{insp}$—patient's time of inspiration
$T_e$—patient's time of expiration To step down the patient's breath rate, a sequence of steps 200 of TLDS 102 operates LLCS 104 in a synchronous mode (S-Mode) for X amount of time (i.e., $T_{insp}^{M}=T_{insp}$ and $T_e^{M}=T_e$) and the patient's average breath rate $BR_p(k)$ is monitored, as shown at steps 202 and 204. That is, the machine is set to follow precisely the patient's breathing pattern. At step 206, once the S-mode operation has been completed, TLDS 102 reduces the target breath rate by a breath rate unit (BRU) below the current average breath rate measured during S-mode and resets a therapy timer $t_h$ to determine a next target breath rate update and the conclusion of therapy time. At step 208 a breath count k is incremented at the end of expiration. Thereafter, at step 210, TLDS 102 resets a timer t, which represents the time spent at the current breath.

At the end of each breath, TLDS 102 determines, at step 212, whether or not the last breath (BR(k)) was at or below (the exemplary) 10 BPM (breaths per minute). If so, then at step 214 the breath period is added to the therapy timer, $t_h$. If the therapy timer has not reached a total time of 10 minutes or more as shown at step 216, then, at step 218, TLDS 102 polls the LLCS to see if there is an updated target breath rate. If so, then $BR_{target}$ is updated at step 220 and a new cycle is started. Otherwise TLDS 102 determines, at step 222 if it is time to update the target breath rate by polling timer t (which indicates the time spent at the current breath rate). More specifically, if the time to update target breath has been reached (i.e., y amount of time has elapsed since the last time target breath rate was updated, or t≧y time), then the target breath rate is again updated according to the following rules implemented by step 224:

1. If the patient is breathing more slowly than the machine (i.e., the current target breath rate is greater than or equal to the patient's average breath rate), then the new target breath rate is updated to the average breath rate minus one BRU (step 226).
2. If the patient is breathing faster than the machine, then the target breath rate is set to the patient's breath rate (step 228). If the values are equal, step 226 is performed to reduce the user's breath rate. The target is set to the patient's rate preferably only when the patient rate is faster than the machine.

More simply put, if the patient is breathing more slowly than the machine, the machine is adjusted to push the patient's breathing to a slower pace. Otherwise, if the patient is breathing faster than the machine, the machine "backs up" and adjusts itself to the breathing rate of the patient.

Finally, if at the end of the breath no action is required (i.e., none of the cases above were executed), then the timer t is reset, and the TLDS waits for the end of another breath. If at step 212 the patient's instantaneous breath rate was not less than 10 BPM, then the breath period is not added to the total therapy time $t_h$ and the process continues with step 216. If the total therapy time $t_h$ is greater than, e.g., 10 minutes as depicted at step 216, then the patient is deemed to have had a breath rate at the desired frequency for at least 10 minutes and the process returns to S-mode, as illustrated by step 230.

Low Level Control System

The target breath rate generated by TLDS 102 is sent to LLCS 104 where it is used to determine the $T_{insp}^M$ and $T_e^M$ to be used on the current breath cycle. To determine the value of $T_{insp}^M$ and $T_e^M$, LLCS 104 uses standard, well-known, integral control equations with anti-windup mechanisms in addition to a state machine mode that chooses adequate control values to provide the maximum comfort to the patient.

Figure 3:
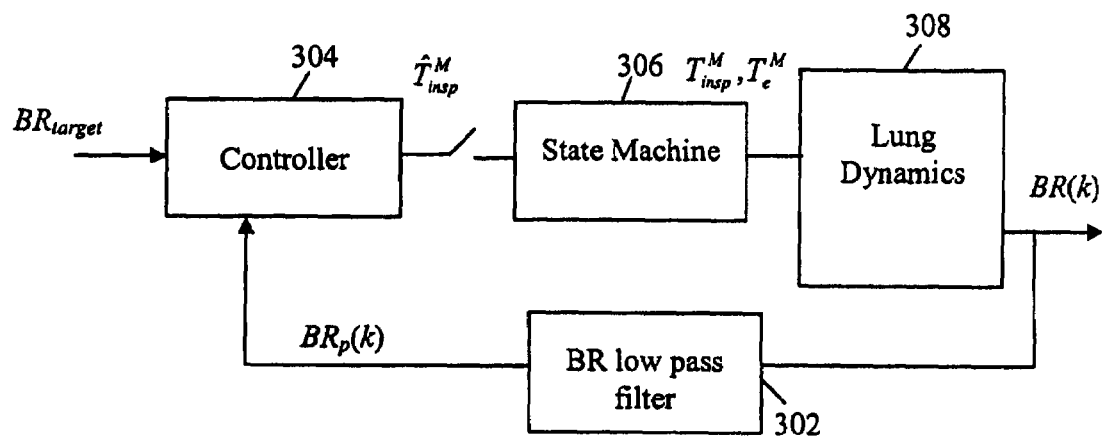
FIG. 3 depicts an exemplary low level control system (LLCS) in accordance with an embodiment of the present invention.

FIG. 3 illustrates the components governing the control mechanism in block diagram form. Specifically, depicted are:

1. Breath rate (BR) low pass filter 302,
2. Controller 304,
3. State Machine Mechanism 306, and
4. Lung Dynamics 308.

Breath rate (BR) low pass filter 302 determines an average breath rate for the last n breaths (by monitoring lung dynamics 308), and provides controller 304 with a measure of the respiratory state of the patient. Controller 304 estimates $\hat{T}_{insp}^M$ that seems adequate for the current breath using the reading of the filter breath rate and the target breath rate. Finally, state machine 306 takes the output of controller 304 as a reference and uses it to compute the actual machine periods of inspiration and expiration states, $T_{insp}^M$ and $T_e^M$, respectively. The detailed equations that express the behavior of these blocks are described below.

To determine the value of $\hat{T}_{insp}^M$, the PB method uses a breath rate controller whose equation resembles an integral controller (see eq. (1) and eq. (2).) An objective of controller 304 is to increase the machine estimated inspiration time $\hat{T}_{insp}^M$ as the error (e(k)) between the current target breath rate and the current low pass filtered patient's breath rate increases as follows:

$$e(k)=BR_{target}(k)-BR_p(k), \quad (1)$$

$$\hat{T}_{insp}^M(k)=K_I e(k)+T_{insp}^M(k-1), \quad (2)$$

In these equations, k is the current breath number, e(k) is the current error signal between current target breath rate $BR_{target}(k)$ and the patient's current breath rate after filtering $BR_p(k)$, and $\hat{T}_{insp}^M(k)$ is the estimated machine time of inspiration to be used by state machine 306.

The BR Low Pass Filter

In one possible embodiment, breath rate low pass filter 302 uses a single FIR digital filter to determine an average breath rate. An exemplary equation governing the behavior of this block is:

$$BR_p(k) = \sum_{m=0}^{N} b_m(BR(k-m)). \quad (3)$$

Where $BR_p(k)$ is the low pass filter signal and BR(k)s are the instantaneous signal samples at breath k. And, $b_m$ is a weighting factor. For instance, $b_m$ may be 1/N for a simple moving average. Alternatively, $b_m$ may be a weighted average.

The State Machine

State Machine 306 determines the actual values of machine inspiration and expiration time to be provided to the patient. These values are determined as follows:

$$T_{insp}^M(k)=\max(\hat{T}_{insp}^M(k),T_{insp}), \quad (4)$$

$$\hat{T}_e^M(k)=(R)T_{insp}^M(k), \text{ and} \quad (5)$$

$$T_e^M(k)=\min(\hat{T}_e^M(k),T(k)-T_{insp}^M(k)). \quad (6)$$

In equations (4), (5) and (6), k represents the current breath, $\hat{T}_{insp}^M(k)$ and $\hat{T}_e^M(k)$ are the estimated machine inspiration and expiration time, $T_{insp}(k)$ is the patient's inspiration time, T(k) is the patient's periodic time (i.e., period of given entire breath) and $T_{insp}^M(k)$ and $T_e^M(k)$ represent the actual machine inspiration and expiration time, respectively.

From equation (4) it is noted that the machine actual inspiration time is determined by the longest time between the controller estimated time and the patient's inspiration time. This mechanism provides a way to encourage patients to elongate their inspiration time. As for the patient's expiration time in equation (6), it is noted that state machine 306 will end expiration based on the shortest time of estimated machine time of expiration ($\hat{T}_e^M(k)$) or patient's time to expiration ($T(k)-T_{insp}^M(k)$). The machine estimated expiration time is, as mentioned before, calculated based on a fixed ratio (R) of the machine time of inspiration $T_{insp}^M(k)$ (see eq. (5).)

Figure 4A:
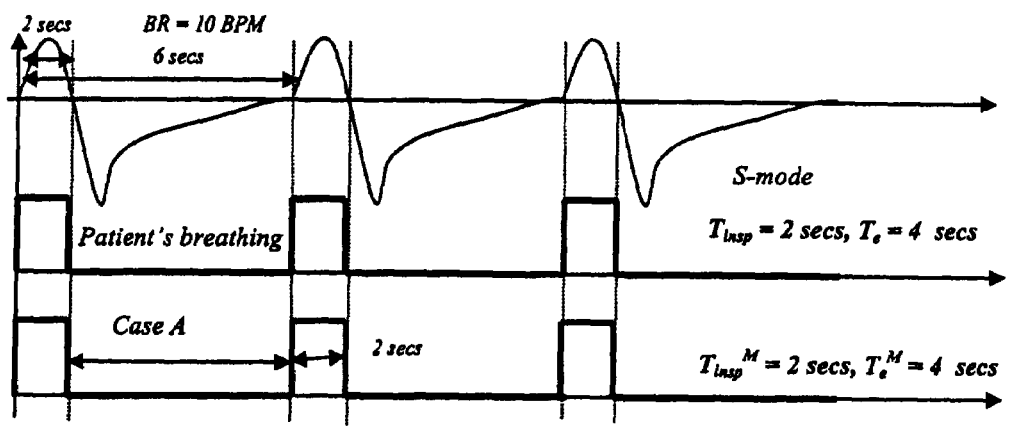
FIGS. 4A-C depict several operating scenarios for the PB method in accordance with an embodiment of the present invention.
Figure 4B:
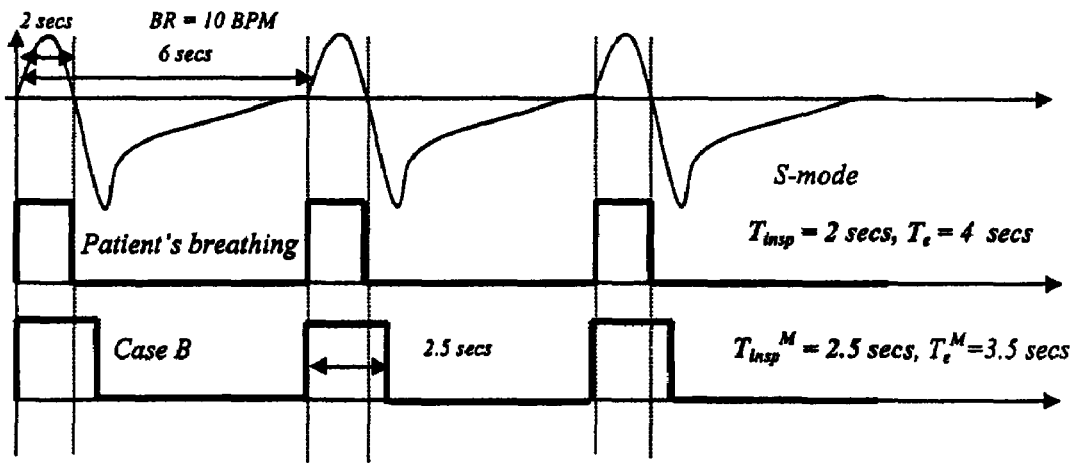
Figure 4C:
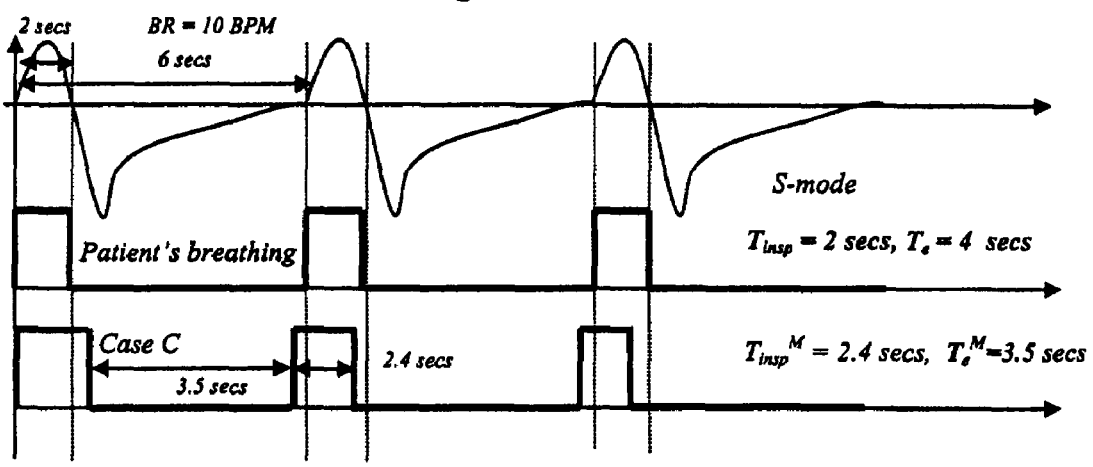

To better understand the dynamics of equations (4)-(6), several scenarios are illustrated in FIGS. 4A-C. In these Figures, the graphs represent a patient breathing at 10 BPM, with $T_{insp}(k)$=2 secs and $T_e(k)$=4 secs.

Case A in FIG. 4A, illustrates when $\hat{T}_{insp}^M(k)<T_{insp}(k)$, making $T_{insp}^M(k)$ equal to $T_{insp}(k)$=2 secs. This case also illustrates when $\hat{T}_e^M(k)>T_e(k)$ and therefore $T_e^M(k)$ equals $T_e(k)$=4 secs. In case A, the machine is substantially perfectly aligned with the patient breathing.

Case B of FIG. 4B illustrates when $\hat{T}_{insp}^M(k)>T_{insp}(k)$. In this case, $T_{insp}^M(k)=\hat{T}_{insp}^M(k)$=2.5 secs, and $T_{insp}(k)$=2.0 secs. Note that the effect is that the patient will be provided IPAP HI pressure for a longer period of time as illustrated in the graph. Finally, case C of FIG. 4C illustrates when $\hat{T}_e^M(k)<T_e(k)$. In this case, $T_e^M(k)$ equals $\hat{T}_e^M(k)$=3.5 secs and the machine will initiate another inspiration period before the patient will actually initiate inspiration.

Note that the essence of the LLCS is to choose between two possible frequencies $f_1$ or $f_2$ on a breath-by-breath basis. The variable $f_1$ is defined by the patient's breath rate (see cases A and B of FIGS. 4A and 4B,) and $f_2$ is defined as a fixed lower frequency determined by fixed ratio (R) (as shown in case C of FIG. 4C.)

When the preset frequency $f_2$ is chosen, the patient's breath rate $f_1$ is slower than the device's current target frequency. In this case, it is desirable that the machine reduce its coaching frequency $f_1$ via the TLDS. In this scenario, state machine 306 sends an update to the target breath rate below the current patient's breath rate ($BR_p(k)$) as shown in FIG. 1 and FIG. 2.

Based on the foregoing, those skilled in the art will appreciate the novel aspects of the embodiments of the PB method. Still other benefits of the PB method are described below.

As explained in detail above, the PB method uses pressure cues to coach the user's breathing pattern to a targeted frequency. As such, devices intended to deliver gases other than room air can also be configured to operate in a similar manner. Examples of such devices include oxygen delivery devices, anesthesia devices, fresh air respirators, and respiratory (or other) drug delivery devices. It should also be appreciated that the cues may be positive pressure, negative pressure, or atmospheric. In addition, the inventors also contemplate that the unique features of the present invention may be incorporated into a stand-alone device which utilizes any humanly perceptible stimulus to cue the user. In addition to pressure based cues as described above, the cues may also be tactile, visual, or sonic.

Also, because the PB method involves tracking patient synchronization with the device delivering pressure cues, it is possible to employ the method to track sleep onset. If, for example, after a period of successfully lowering breath rate using pressure cues from the device, a patient is no longer able to synchronize with the PB method (despite several iterations attempting to do so), the device can assume the user is asleep and no longer cognitively able to interact with the breathing coach. In such cases, the machine can provide an accurate assessment of sleep onset time. This feature may represent a valuable commodity to the health care provider since it can provide a more accurate assessment of true sleep time with the devices versus merely "machine run time."

As noted previously, the PB method incorporates a breathing coach that actively works to reduce the user's breath rate. There is both scientific and anecdotal knowledge supporting the notion that such measures can reduce stress and induce a more relaxed state. Qigong, yoga, and other deep-breathing exercises are used by millions for stress relief and many other purposes. The scientific merit of such behavior modification has become well established in recent years.

For similar reasons, the PB method can be used in the treatment of chronic pain syndrome. The mechanisms through which the device works for indication are not fully understood, but may be related to the changes in baroreflex sensitivity that mediate the noted effects on hypertension.

Also for similar reasons, the PB method may be use in lieu of or in addition to anxiolytics to combat anxiety.

Previous evidence has suggested that deep breathing exercises can produce effective reductions in cholesterol associated with hypertension and stress. It is thought that the mechanisms underlying these effects may be related to central changes associated with baroreflex sensitivity following several weeks of deep breathing intervention. Whether the changes in cholesterol levels are the result of reduced hypertension and stress levels or some parallel phenomena are unknown.

The PB method may also be effective in weight loss programs.

Likewise, the PB method may be helpful in the detection and treatment of Attention Deficit Hyperactivity Disorder (ADHD).

Also, the PB method may be helpful in the detection and treatment of Panic Disorder.

In addition, because of the propensity of the techniques of the PB method to induce relaxation and reduce stress, it may also be desirable to monitor the level of "relaxation" felt by the user. Such measurements might include:

Sympathetic tone (tonometry)
Non-invasive Blood Pressure (via cuff)
Plethysmography
Pulse Transit Time
Galvanic Skin Response
Pupillary diameter
Muscle Sympathetic Nerve Activity (MSNA)

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method of adjusting a breathing rate of a self-ventilating user, the method comprising:
    monitoring respiration of a self-ventilating user and determining a user breathing frequency of said self-ventilating user, wherein respiration comprises an inspiration portion and an expiration portion;
    setting a target breathing frequency at or below the user breathing frequency;
    providing breathing cues to the self-ventilating user to breathe at the target breathing frequency by supplying a high positive air pressure to said self-ventilating user during said inspiration portion and a low positive air pressure during said expiration portion in substantial synchronicity with respiration at the target breathing frequency;
    subsequent to providing breathing cues to the self-ventilating user to breathe at the target breathing frequency, determining an undated user breathing frequency of the self-ventilating user;
    comparing said updated user breathing frequency with the target breathing frequency; and
    increasing the target breathing frequency if the updated user breathing frequency of said self-ventilating user is greater than the target breathing frequency.

2. The method of claim 1, further comprising adjusting the time over which said low positive pressure air pressure is supplied to said self-ventilating user to achieve a predetermined ratio between the time over which said high positive air pressure is supplied to said self-ventilating user and the time over which said low positive pressure air pressure is supplied to said self-ventilating user.

3. The method of claim 1, wherein the time over which said low positive pressure air pressure is supplied to said self-ventilating user is set as a minimum of an estimated expiration time and said self-ventilating user's actual expiration time.

4. The method of claim 1, further comprising incrementally lowering the target breathing rate toward a goal breathing rate if the updated breathing frequency is less than or equal to the target breathing rate.

5. The method of claim 4, further comprising keeping track of a therapy time and comparing said therapy time to a predetermined threshold amount of therapy time, wherein therapy time is time during which the target breathing rate is equal to or less than the goal breathing rate.

6. The method of claim 4, wherein the goal breathing rate is about 10 breaths per minute.

7. The method of claim 1, further comprising determining how long said self-ventilating user is breathing at a given breathing frequency.

8. The method of claim 1, wherein a top level driving system supplies said target breathing frequency to a low level control system that controls said high positive air pressure and said low positive air pressure.

9. The method of claim 4, wherein providing breathing cues to the self-ventilating user to breathe at the target breathing frequency subsequent to the incremental lowering of the target breathing frequency comprises increasing a time over which said high positive air pressure is supplied to said self-ventilating user.

10. The method of claim 1, further comprising computing an average breath rate for said self-ventilating user.

11. The method of claim 1, further comprising computing a difference between said target breathing frequency and said current user breathing frequency.

12. The method of claim 1, further comprising supplying a gas other than room air.

13. The method of claim 1, further comprising detecting onset of a sleeping state of the self-ventilating user based on the self-ventilating user's responsiveness to changes in the target breathing frequency.

14. A method for adjusting a breathing rate of a self-ventilating person, the method comprising:
monitoring a current breath rate of a self-ventilating person;
obtaining a target breath rate that is different than the breath rate of the self-ventilating person; and
providing breathing cues to the self-ventilating person that prompt the self-ventilating person to breathe at the target breath rate, wherein providing breathing cues to the self-ventilating person comprises adjusting one or more parameters of a flow of gas directed to the airway of the self-ventilating person.

15. The method of claim 14, wherein monitoring the self-ventilating person's breath rate comprises selectively filtering signals indicative of breathing dynamics of the self-ventilating person.

16. The method of claim 14, wherein monitoring the breath rate of the self-ventilating person comprises determining the length of an inspiration period of the self-ventilating person, wherein obtaining the target breath rate comprises obtaining a length of an estimated inspiration period, and wherein providing breathing cues to the self-ventilating person comprises providing breathing cues to the self-ventilating person prompting the self-ventilating person to inhale for an inspiration period having a length that corresponds to the longer of the inspiration period of the self-ventilating person or the estimated inspiration period.

17. The method of claim 14, wherein monitoring the breath rate of the self-ventilating person comprises determining the length of an expiration period of the self-ventilating person, wherein obtaining the target breath rate comprises obtaining a length of an estimated expiration period, and wherein providing breathing cues to the self-ventilating person comprises providing breathing cues to the self-ventilating person promoting the self-ventilating person to exhale for an expiration period having a length that corresponds to the shorter of the expiration period of the self-ventilating person or the estimated expiration period.

18. The method of claim 14, wherein the flow of gas directed to the airway of the self-ventilating person as breathing cues is directed to the airway of the subject by a bi-level positive air pressure device.

19. The method of claim 14, wherein the one or more parameters of the flow of gas directed to the airway of the self-ventilating person as breathing cues include one or both of flow rate and/or pressure.

20. A method for controlling a bi-level positive air pressure (BiPAP) device, comprising:
setting a machine inspiration time as a maximum of an estimated inspiration time and an actual inspiration time of a user;
setting a machine expiration time as a minimum of an estimated expiration time and a difference between a period of a breath of the user and the machine expiration time; and
using the machine inspiration time and the machine expiration time to control respective HI and LO positive pressure timings in the BiPAP device.

21. The method of claim 20, further comprising keeping track of a therapy time and comparing said therapy time to a predetermined maximum therapy time.

22. The method of claim 20, further comprising increasing, in a predetermined manner, the estimated inspiration time.

23. The method of claim 20, further comprising determining how long a user of the BiPAP device is breathing at a given breathing frequency.

* * * * *